United States Patent [19]
Wittenbrink et al.

[11] Patent Number: 6,075,061
[45] Date of Patent: Jun. 13, 2000

[54] INTEGRATED PROCESS FOR CONVERTING NATURAL GAS AND GAS FIELD CONDENSATE INTO HIGH VALUED LIQUID PRODUCTS (LAW713)

[75] Inventors: Robert Jay Wittenbrink, Baton Rouge, La.; Bruce Randall Cook, Pittstown; Paul Joseph Berlowitz, East Windsor, both of N.J.

[73] Assignee: Exxon Research and Engineering Company, Florham Park, N.J.

[21] Appl. No.: 09/108,102

[22] Filed: Jun. 30, 1998

[51] Int. Cl.⁷ .............................. C07C 27/00; C07C 5/13; C10G 35/06
[52] U.S. Cl. ........................... 518/715; 518/700; 518/702; 518/706; 518/714; 585/734; 585/750; 208/136
[58] Field of Search .................................... 518/702, 706, 518/700, 714, 715; 585/734, 750; 208/136, 137

[56] References Cited

U.S. PATENT DOCUMENTS

| | | | |
|---|---|---|---|
| 5,378,348 | 1/1995 | Davis et al. | 208/27 |
| 5,750,819 | 5/1998 | Wittenbrink et al. | 585/734 |

FOREIGN PATENT DOCUMENTS

| | | | |
|---|---|---|---|
| 2178756 | 2/1987 | United Kingdom | C07C 1/04 |
| 9703750 | 2/1997 | WIPO | B01J 21/12 |
| 9728106 | 8/1997 | WIPO | . |
| 9819792 | 5/1998 | WIPO | B01J 23/885 |
| 9910098 | 3/1999 | WIPO | B01J 23/755 |

*Primary Examiner*—Johann Richter
*Assistant Examiner*—J. Parsa
*Attorney, Agent, or Firm*—Estelle C. Bakun

[57] ABSTRACT

The instant invention is directed to an integrated process for producing a hydroisomerate in the presence of sulfur comprising the steps of (a) separating a natural gas into a first stream comprising a $C_5+$ gas field condensate containing sulfur and a second stream comprising said natural gas having said a $C_5+$ gas field condensate removed therefrom, (b) removing sulfur from said second stream, (c) subjecting said second stream to a synthesis gas generation process to produce synthesis gas; (d) subjecting said synthesis gas to a hydrocarbon synthesis process to produce hydrocarbons, (e) hydrotreating and hydroisomerizing said hydrocarbons of step (d) in the presence of said first stream over a catalyst having an acidic functionality and comprising a Group VIII non-noble metal or tungsten and a hydrocracking suppressant, wherein said hydrocracking suppressant is selected from the group consisting of Group IB metal, sulfur and mixtures thereof, and wherein when said hydrocracking suppressant is sulfur, said acidic functionality is an amorphous refractory oxide.

14 Claims, 1 Drawing Sheet

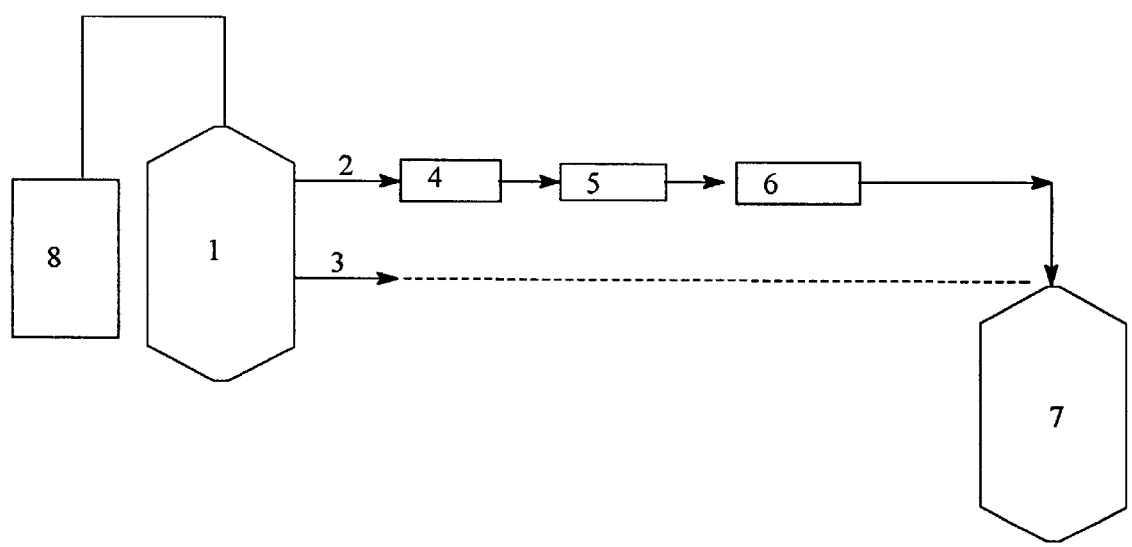
FIGURE

6,075,061

INTEGRATED PROCESS FOR CONVERTING NATURAL GAS AND GAS FIELD CONDENSATE INTO HIGH VALUED LIQUID PRODUCTS (LAW713)

FIELD OF THE INVENTION

BACKGROUND OF THE INVENTION

Isomerization processes generally require the removal, e.g., by hydrotreating, of sulfur and nitrogen compounds that can rapidly deactivate or poison the isomerization process catalyst. Consequently, feeds to be isomerized are first contacted with a sulfur tolerant catalyst in the presence of hydrogen to minimize the amount of sulfur in the feed.

Additionally, isomerization processes, particularly those carried out on Fischer-Tropsch derived feed stocks in the presence of hydrogen, are effected with unsulfided catalysts. As a consequence, hydrogenolysis, e.g., hydrocracking, occurs in the processing and produces significant amounts of gaseous products, e.g., methane or $C_1$–$C_4$ hydrocarbons. A process, therefore, that can eliminate or substantially reduce the hydrogenolysis aspect of the process, even in the presence of sulfur, can be more efficient and more economic because of increased yields of desired products and decreased yields of gaseous products.

Natural gas fields typically contain a significant amount of $C_5$+ material, which is liquid at ambient conditions. These liquids must be upgraded (e.g., sulfur removed) if they are to be used as liquid petroleum fuels. An integrated process, which can upgrade both the natural gas field condensate and the Fischer-Tropsch liquids into high valued liquid petroleum products in a single unit, would be advantageous.

Currently, the gas field condensate is separated from the gaseous product and upgraded in separate vessels to remove sulfur and other undesirable materials in conventional hydrotreating units or in Merox units.

SUMMARY OF THE INVENTION

The instant invention is directed to an integrated process for converting natural gas and gas field condensate into high valued liquid products comprising the steps of:

(a) separating a natural gas into a first stream comprising a $C_5$+ gas field condensate containing sulfur and a second stream comprising said natural gas having said $C_5$+ gas field condensate removed therefrom;

(b) removing sulfur from said second stream;

(c) subjecting said second stream to a synthesis gas generation process to produce synthesis gas;

(d) subjecting said synthesis gas to a hydrocarbon synthesis process to produce hydrocarbons;

(e) hydrotreating and hydroisomerizing said hydrocarbons of step (d) in the presence of said first stream over a catalyst having an acidic functionality and comprising a Group VIII non-noble metal, a Group VI metal, and a hydrocracking suppressant, wherein said hydrocracking suppressant is selected from the group consisting of Group IB metal, sulfur and mixtures thereof and wherein when said hydrocracking suppressant is sulfur, said acidic functionality is an amorphous metal oxide or mixture of metal oxides.

BRIEF DESCRIPTION OF THE FIGURES

The FIGURE is an illustration of the integrated process herein described as follows: (1) is a separator, (2) is a $C_1$14 $C_4$ gas, (3) a $C_5$+ gas field condensate, (4) gas treating and sulfur recovery, (5) synthesis gas generator, (6) a hydrocarbon synthesis unit (Fischer-Tropsch), (7) a hydroisomerization unit, and (8) a natural gas well.

DETAILED DESCRIPTION OF THE INVENTION

The instant process is directed to an integrated process for converting natural gas and gas field condensate into high valued liquid products. The process is beneficial because it allows for removal of sulfur present in the natural gas prior to a synthesis gas generation and subsequent hydrocarbon synthesis step (HCS), and reintroduction of the sulfur containing stream during a latter hydroisomerization (HI) step. Such a process affords a sulfur free feed to the very sulfur sensitive HCS step, while allowing for addition of sulfur to the HI step to help reduce hydrocracking and to remove troublesome sulfur from the $C_5$+ gas condensate stream. Beneficially, the process of the instant invention decreases hydrogenolysis during the HI step by at least about 60%, preferably at least about 80%, and most preferably at least about 95%.

A gas field produces a $C_1$+ stream. Typically a $C_1$–$C_4$ gas stream is concentrated and purified by known techniques such as FLEXSORB® followed by ZnO and/or massive Ni to remove sulfur. Other techniques known to those skilled in the art for sulfur removal may also be utilized. The $CH_4$ is then reacted with oxygen to produce synthesis gas. The synthesis gas is then reacted in a hydrocarbon synthesis reactor, preferably a Fischer-Tropsch reactor to produce long chain paraffins. It is known that Fischer-Tropsch catalysts are very sensitive to sulfur and readily become poisoned by it. However, the hydroisomerization catalysts utilized herein are not sulfur sensitive but instead are enhanced by the presence of sulfur. The instant process allows for an integrated process to be conducted whereby the sulfur present in the natural gas stream is absent during hydrocarbon synthesis, and present during hydroisomerization. The process alleviates the need to add an additional sulfur removal step, e.g., hydrotreating or Merox, for the $C_5$+ gas condensate stream.

In accordance with this invention the hydroisomerization step (d) is conducted in the presence of hydrogen and a catalyst comprising a Group VIII non-noble metal, a Group VI metal, and a hydrocracking suppressant. The hydrocracking suppressant may be either a Group IB metal or a source of sulfur, usually in the form of a sulfided catalytically active metal, or a Group IB metal and a source of sulfur. Hydrocracking suppression can be effectively measured by suppressing methane, since hydrocracking most easily occurs through terminal cracking. Each of the steps in the process are conducted at conditions commonly known to the skilled artisan for the particular step being conducted. For example, the hydroisomerization step is conducted under hydroisomerization conditions, and the Fischer-Tropsch step is conducted under Fischer-Tropsch synthesis conditions. All conditions are well known in the art. Preferably, the hydrocarbon synthesis step (d) will be a Fischer Tropsch process utilizing a cobalt catalyst, more preferably a cobalt-rhenium catalyst operating at high alpha values, e.g., greater than 0.90 such that a high percentage of Fischer-Tropsch wax will be produced. The Fischer-Tropsch feeds typically contain 0.1 wppm of sulfur or less. Generally, the hydroisomerization process of this invention will lead to methane yields of less than about 5 wt % based on total 700° F.+ conversion, preferably less than about 2 wt %, more preferably less than about 1 wt %, and still more preferably less than about 0.5 wt %. In a preferred embodiment, the catalyst also contains effective amounts of a Group VI metal.

Typical hydroisomerization conditions are well known in the literature and can vary widely. For example, broad and preferred ranges for these conditions are shown in the following table:

| CONDITION | BROAD | PREFERRED | MOST PREFERRED |
|---|---|---|---|
| Temperature, ° F. | 300–900 (149–482° C.) | 550–750 (288–399° C.) | 675–750 |
| Total pressure, psig | 300–2500 | 500–1200 | 700–1000 |
| Hydrogen Treat Rate, SCF/B | 500–5000 | 2000–4000 | 2000–3000 |

Each of the steps in the integrated process are run under conditions known to the skilled artisan. For example, the hydrocarbon synthesis step, if a Fischer-Tropsch synthesis, would be run under Fischer-Tropsch conditions. Likewise, the synthesis gas generation step will be run under synthesis gas generation conditions.

The catalysts useful in the hydroisomerization step of the instant process preferably contain an acid function as well as the hydrocracking suppressant. The hydrocracking suppressant may be either a Group IB metal, e.g., preferably copper, in amounts of about 0.1–10 wt %, or a source of sulfur, or both. The source of sulfur can be provided by pre-sulfiding the catalyst by known methods, for example, by treatment with hydrogen sulfide until breakthrough occurs. Catalysts containing sulfur typically have at least about 0.01 wt % sulfur, preferably about 0.01 to 20% sulfur, preferably 0.1 to 10 wt %.

The Group VIII non-noble metals may include nickel and cobalt, preferably cobalt. The Group VIII metal is usually present in catalytically effective amounts, that is, ranging from 0.5 to 20 wt %. Preferably, a Group VI metal is incorporated into the catalyst, e.g., molybdenum, in amounts of about 1–20 wt %.

The acid functionality can be furnished by a support with which the catalytic metal or metals can be composited in well known methods. The support can be any amorphous refractory oxide or mixture of amorphous refractory oxides or zeolites or mixtures thereof. Preferred supports include silica, alumina, silica-alumina, silica-alumina-phosphates, titania, zirconia, vanadia and other Group III, IV, V or VI oxides, as well as Y sieves, such as ultra stable Y sieves. Preferred supports include alumina and silica-alumina, more preferably silica-alumina where the silica concentration of the bulk support is less than about 50 wt %, preferably less than about 35 wt %, more preferably 15–30 wt %. When alumina is used as the support, small amounts of chlorine or fluorine may be incorporated into the support to provide the acid functionality. Preferably, when the hydrocracking suppressant is sulfur, said acidic functionality is an amorphous metal oxide or mixture of amorphous metal oxides.

A preferred supported catalyst has surface areas in the range of about 180–400 m$^2$/gm, preferably 230–350 m$^2$/gm, and a pore volume of 0.3 to 1.0 ml/gm, preferably 0.35 to 0.75 ml/gm, a bulk density of about 0.5–1.0 g/ml, and a side crushing strength of about 0.8 to 3.5 kg/mm.

The preparation of preferred amorphous silica-alumina microspheres for use as supports is described in Ryland, Lloyd B., Tamele, M. W., and Wilson, J. N., Cracking Catalysts, Catalysis; Volume VII, Ed. Paul H. Emmett, Reinhold Publishing Corporation, New York, 1960.

During hydroisomerization, the 700° F.+ conversion to 700° F.− ranges from about 20–80%, preferably 30–70%, more preferably about 40–60%; and essentially all olefins and oxygenated products from the Fischer-Tropsch reaction are hydrogenated. The amount of hydrodesulfurization will also be significant, depending on the type of sulfur molecules present. Typically, the sulfur compounds in gas field condensate are relatively easy to remove sulfur compounds, e.g., mercaptans, sulfides, and disulfides, and the level of sulfur in the resulting product therefore is typically very low, e.g., less than 300 wppm sulfur.

The feed to step (d) of the process will be a Fischer-Tropsch wax or reaction product and the $C_5$+ gas field condensate stream. The sulfur in the $C_5$+ condensate acts to keep the HI catalyst sulfided which significantly decreases undesirable hydrogenolysis reactions while the HI step simultaneously lowers the sulfur level in the $C_5$+ condensate and, hence, the liquid product.

The HI catalyst can be prepared by any well known method, e.g., impregnation with an aqueous salt, incipient wetness technique, followed by drying at about 125–150° C. for 1–24 hours, calcination at about 300–500° C. for about 1–6 hours, reduction by treatment with a hydrogen or a hydrogen containing gas, and, if desired, sulfiding by treatment with a sulfur containing gas, e.g., $H_2S$ at elevated temperatures. The catalyst will then have about 0.01 to 10 wt % sulfur. The metals can be composited or added to the catalyst either serially, in any order, or by co-impregnation of two or more metals.

The following examples will serve to illustrate, but not limit this invention.

EXAMPLE 1

A commercial Co—Mo catalyst on a $SiO_2$—$Al_2O_3$ support containing 20–30 wt % bulk silica was reduced at 370° C. for 3 hours in hydrogen. The catalyst was used to hydroisomerize n-heptane as a model compound representing the more refractory paraffins present in condensate. The results of the isomerization test are found in the following table.

EXAMPLE 2

The Co—Mo catalyst of Example 1 was impregnated with an aqueous solution of copper nitrate to introduce 0.3 wt % Cu. The catalyst was calcined in air at 370° C. and reduced in hydrogen at 370° C. for 3 hours. The Co—Mo—Cu catalyst was used to hydroisomerize n-heptane. The results are presented in the table below.

EXAMPLE 3

The Co—Mo catalyst of Example 1 was reduced in hydrogen at 370° C. for 3 hours and breakthrough sulfided with dilute $H_2S$ in $H_2$ at 370° C. The catalyst was $H_2$ stripped at the same temperature for 2 hours to remove any chemisorbed $H_2S$. The Co—Mo—S catalyst was used to hydroisomerize n-heptane. The results are included in the following table.

The catalyst of Example 1, while active for hydroisomerization, has extremely high hydrocracking activity as evidenced by very high methane and n-butane yields and the destruction of normal and isoheptanes. Liquid yield is decreased to a value <70 wt %.

The HI catalysts of this invention, Co—Mo—Cu and Co—Mo—S, the catalysts of Examples 2 and 3, are preferred hydroisomerization catalysts on the basis of higher selectivity to isomerized product and substantially decreased hydrocracking activity. In both cases the yields of liquid product exceed 92 wt %, and the formation of isoheptanes is roughly 40% greater than that of Example 1. While not shown in the table, the combination of sulfur with Cu would offer additional yield and selectivity credits relative to those of Examples 2 and 3.

ISOMERIZATION OF HEPTANE WITH
SULFIDED Co—Mo AND Co—Mo—Cu CATALYSTS
n-Heptane, 425° C., 100 psig, 5 W/H/W, $H_2$/Oil = 6

| EXAMPLE Catalyst | 1 Co—Mo | 2 Co—Mo—Cu | 3 Co—Mo—S |
|---|---|---|---|
| $C_1$ | 6.4 | 1.4 | 0.2 |
| i-$C_4$ | 0.5 | 0.3 | 0.1 |
| n-$C_4$ | 4.0 | 0.8 | 1.0 |
| n-$C_7$ | 56.3 | 77.5 | 77.7 |
| 2,4-DMP | 0.4 | 0.6 | 0.4 |
| 2-Me—Hex | 4.6 | 6.2 | 6.5 |
| 3-Me—Hex | 6.4 | 8.6 | 9.6 |
| i-$C_7$'s | 11.4 | 15.4 | 16.6 |

Fischer-Tropsch Feed Preparation

EXAMPLE 4

A mixture of hydrogen and carbon monoxide synthesis gas ($H_2$/CO=2.0–2.2) was converted to heavy paraffins in a slurry Fischer-Tropsch reactor. A titania supported cobalt rhenium catalyst was utilized for the Fischer-Tropsch reaction. The reaction was conducted at about 400–450° F., 280 psig, and the feed was introduced at a linear velocity of 12 to 17.5 cm/sec. The kinetic alpha of the Fischer-Tropsch product was 0.92. The Fischer-Tropsch wax feed was withdrawn directly from the slurry reactor. The boiling point distribution and oxygenate content of this wax is given in Table 1.

TABLE 2

Boiling Point Distribution of Fischer-Tropsch Wax Fraction

| Boiling Range | Reactor Wax |
|---|---|
| IBP–350° F. | 0.00 |
| 350–500° F. | 0.70 |
| 500–700° F. | 20.48 |
| 700° F.+ | 78.82 |

EXAMPLE 5

A sample of gas field condensate (25 vol %) was added to the Fischer-Tropsch wax (75%) prepared in Example 4. This feed was then used in the hydroisomerization studies using the catalysts described in Examples 2 and 3. Analyses of this feed are listed in Table 3.

TABLE 3

Properties of Fischer-Tropsch Wax/Gas Field Condensate Feed

| Boiling Range | Reactor Wax |
|---|---|
| IBP–350° F. | 11.72 |
| 350–500° F. | 9.22 |
| 500–700° F. | 19.46 |
| 700° F.+ | 59.60 |
| Sulfur, wppm | 625 |

Hydroisomerization Studies

EXAMPLE 6

The catalysts described in Examples 1, 2 and 3 were then tested for wax hydroisomerization and condensate hydrodesulfurization on the feeds described in Example 4 (Fischer-Tropsch reactor wax) and Example 5 (Fischer-Tropsch reactor wax plus gas field condensate). Screening was carried out in a small up-flow pilot plant using procedures developed previously in connection with HCS wax hydroisomerization studies. The catalysts were evaluated at 750 psig $H_2$, 1.00 LHSV, and with a hydrogen treat rate of 2500 SCF/B. A 10 mL charge of catalyst crushed and screened to 14/35 mesh was employed in all cases. Balances were typically collected at 24–72 hour intervals.

Product distributions were determined by both simulated gas chromatography (i.e., GCD) and 15/5 distillation. Gas samples were collected in gas collection bombs just prior to end of each balance and analyzed using mass spectroscopy. 700° F.+ wax conversion was calculated using the following equation:

$$700° \text{ F.+ Conversion} = [1-(700° \text{ F.+ in product}/700° \text{ F.+ in feed})] \times 100$$

The reaction temperature was adjusted to provide about 50% 700° F.+ wax conversion levels. The results are summarized in Table 4. Clearly, the process and catalyst system is very effective at both Fischer-Tropsch wax hydroisomerization and condensate hydrodesulfurization. At the conditions studied the sulfur removal was significant. In addition, there is a synergistic effect in that the sulfur, which is present in the gas field condensate, significantly reduces the hydrogenolysis activity of the catalyst as evidenced by the lower $C_1$–$C_2$ yields. Addition of copper to the system further reduces the hydrogenoylsis activity while maintaining the hydroisomerization activity.

TABLE 4

Hydroisomerization and Hydrodesulfurization Results

| Catalyst Example # Feed | 1 Co—Mo F-T Wax | 2* Co—Mo—Cu F-T Wax + Gas Field Condensate | 3 Co—Mo—S |
|---|---|---|---|
| Example # | 4 | 5 | 5 |
| 700° F.+ Wax Conv., % | 53.8 | 51.2 | 56.5 |
| Yields, wt % | | | |
| $C_1$–$C_2$ | 1.21 | 0.08 | 0.23 |
| $C_3$–$C_4$ | 1.43 | 1.06 | 1.21 |
| $C_5$-320° F. | 9.05 | 6.71 | 7.68 |
| 320–500° F. | 13.11 | 30.07 | 31.16 |
| 500–700° F. | 38.77 | 32.97 | 33.81 |
| 700° F.+ | 36.43 | 29.11 | 25.91 |
| Sulfur, wppm | <0.1 | 25 | 46 |

*This catalyst would be equivalent to Co—Mo—Cu—S as sulfur in the feed would act as a sulfiding agent.

What is claimed:

1. An integrated process for producing a hydroisomerate in the presence of sulfur comprising the steps of:
   (a) separating a natural gas into a first stream comprising a $C_5$+ gas field condensate containing sulfur and a second stream comprising said natural gas having said a $C_5$+ gas field condensate removed therefrom;
   (b) removing sulfur from said second stream;
   (c) subjecting said second stream to a synthesis gas generation process to produce synthesis gas;
   (d) subjecting said synthesis gas to a hydrocarbon synthesis process to produce hydrocarbons;

(e) hydrotreating and hydroisomerizing said hydrocarbons of step (d) in the presence of said first stream over a catalyst having an acidic functionality and comprising a Group VIII non-noble metal, a Group VI metal, and a hydrocracking suppressant, wherein said hydrocracking suppressant is selected from the group consisting of Group IB metal, sulfur and mixtures thereof.

2. The process of claim 1 wherein the suppressant is a Group IB metal.

3. The process of claim 1 wherein the suppressant is in the form of a pre-sulfided catalyst.

4. The process of claim 1 wherein the catalyst comprises cobalt and molybdenum in catalytically effective amounts.

5. The process of claim 4 wherein the acidic component is in the form of a silica-alumina support.

6. The process of claim 5 wherein the silica content is less than about 50 wt %.

7. The process of claim 6 wherein the silica content is about 15–30 wt %.

8. The process of claim 3 wherein sulfur is present on the catalyst in an amount of about 0.1–10 wt %.

9. The process of claim 1 wherein when said hydrocracking suppressant is a Group IB metal, said acidic functionality is an amorphous refractory oxide.

10. The process of claim 1 wherein said hydrocarbon synthesis step (c) is a feed is a Fischer-Tropsch synthesis.

11. The process of claim 1 wherein when said hydrocracking suppressant is sulfur, said acidic functionality is an amorphous refractory oxide.

12. The process of claim 1 wherein hydrogenolysis in step (e) is decreased by at least about 60%.

13. The process of claim 1 wherein hydrogenolysis in step (e) is decreased by at least about 80%.

14. The process of claim 1 wherein hydrogenolysis in step (e) is decreased by at least about 95%.

* * * * *